(12) United States Patent
Mao et al.

(10) Patent No.: US 9,199,002 B2
(45) Date of Patent: Dec. 1, 2015

(54) HYBRID SOFT TISSUE IMPLANTS FROM PROGENITOR CELLS AND BIOMATERIALS

(75) Inventors: Jeremy J. Mao, Closter, NJ (US); Eduardo K. Moioli, Coral Springs, FL (US)

(73) Assignee: The Trustees of Columbia University in the City of New York, New York, NY (US)

( * ) Notice: Subject to any disclaimer, the term of this patent is extended or adjusted under 35 U.S.C. 154(b) by 431 days.

(21) Appl. No.: 12/601,793

(22) PCT Filed: May 23, 2008

(86) PCT No.: PCT/US2008/064745
§ 371 (c)(1),
(2), (4) Date: Jul. 28, 2010

(87) PCT Pub. No.: WO2008/148026
PCT Pub. Date: Dec. 4, 2008

(65) Prior Publication Data
US 2010/0305696 A1    Dec. 2, 2010

Related U.S. Application Data

(60) Provisional application No. 60/939,961, filed on May 24, 2007.

(51) Int. Cl.
*A61F 2/12*      (2006.01)
*A61L 27/38*     (2006.01)
(Continued)

(52) U.S. Cl.
CPC . *A61L 27/38* (2013.01); *A61F 2/12* (2013.01); *A61L 27/18* (2013.01); *A61L 27/222* (2013.01);
(Continued)

(58) Field of Classification Search
CPC ....... A61L 27/222; A61L 27/52; A61L 27/56; A61L 27/18; A61L 27/38; A61L 27/3886; A61F 2/12; C12N 5/0653
USPC ........................ 623/8, 23.72–23.76; 427/2.22, 427/2.24–2.26, 2.28, 243–247
See application file for complete search history.

(56) References Cited

U.S. PATENT DOCUMENTS 3,986,213 A * 10/1976 Lynch ................................ 623/8
5,522,896 A * 6/1996 Prescott ...................... 623/23.56
(Continued)

FOREIGN PATENT DOCUMENTS

EP           1466633 A1    10/2004
EP           1656969 A2     5/2006
WO    WO 2006004951 A2 *   1/2006             A61L 27/38

OTHER PUBLICATIONS

Hammond et al. "Morphologic Analysis of Tissue-Expander Shape Using a Biomechanical Model". Plastic and Reconstructive Surgery 92(1993): 255-259.*

(Continued)

*Primary Examiner* — Andrew Iwamaye
(74) *Attorney, Agent, or Firm* — Dentons US LLP

(57) ABSTRACT

Provided are hybrid soft tissue constructs comprising a core material, a biomaterial matrix and mammalian cells. Also provided are methods of augmenting or reconstructing a soft tissue of a mammal. Additionally, methods of forming a hybrid soft tissue construct are provided. The use of the above constructs for augmenting or reconstructing a soft tissue of a mammal are further provided. Additionally provided is the use of the above constructs for the manufacture of a medicament for augmenting or reconstructing a soft tissue of a mammal.

17 Claims, 6 Drawing Sheets

(51) Int. Cl.

| | |
|---|---|
| A61L 27/52 | (2006.01) |
| A61L 27/56 | (2006.01) |
| A61L 27/22 | (2006.01) |
| A61L 27/18 | (2006.01) |
| C12N 5/077 | (2010.01) |

(52) U.S. Cl.
CPC ............. *A61L 27/3886* (2013.01); *A61L 27/52* (2013.01); *A61L 27/56* (2013.01); *C12N 5/0653* (2013.01); *A61F 2210/0061* (2013.01); *A61F 2210/0076* (2013.01); *A61F 2230/0095* (2013.01); *A61F 2310/00383* (2013.01); *A61F 2310/00994* (2013.01); *C12N 2533/30* (2013.01)

(56) References Cited

U.S. PATENT DOCUMENTS

| | | | | |
|---|---|---|---|---|
| 5,716,404 | A | * | 2/1998 | Vacanti et al. ..................... 623/8 |
| 5,869,080 | A | * | 2/1999 | McGregor et al. ............. 424/426 |
| 5,876,452 | A | * | 3/1999 | Athanasiou et al. ....... 623/23.72 |
| 6,328,762 | B1 | * | 12/2001 | Anderson et al. ............ 623/1.41 |
| 6,410,044 | B1 | * | 6/2002 | Chudzik et al. ............... 424/423 |
| 6,582,715 | B1 | * | 6/2003 | Barry et al. ................... 424/422 |
| 6,913,626 | B2 | * | 7/2005 | McGhan ..................... 623/23.73 |
| 6,969,400 | B2 | * | 11/2005 | Rhee et al. .................. 623/11.11 |
| 6,991,652 | B2 | * | 1/2006 | Burg ................................. 623/8 |
| 7,022,135 | B2 | * | 4/2006 | Zilla et al. .................... 623/1.39 |
| 7,094,418 | B2 | * | 8/2006 | Chudzik et al. ............... 424/423 |
| 7,176,256 | B2 | * | 2/2007 | Rhee et al. ..................... 525/54.1 |
| 7,534,451 | B2 | * | 5/2009 | Erbe et al. ...................... 424/484 |
| 2002/0106352 | A1 | | 8/2002 | Amir et al. |
| 2003/0036803 | A1 | * | 2/2003 | McGhan ..................... 623/23.71 |
| 2003/0045927 | A1 | * | 3/2003 | Zilla et al. .................... 623/1.38 |
| 2003/0099682 | A1 | * | 5/2003 | Moussy et al. ................ 424/423 |
| 2003/0220696 | A1 | * | 11/2003 | Levine et al. ............. 623/17.17 |
| 2005/0038515 | A1 | * | 2/2005 | Kunzler ...................... 623/17.13 |
| 2005/0090901 | A1 | * | 4/2005 | Studer ........................ 623/17.12 |
| 2005/0107868 | A1 | * | 5/2005 | Nakayama et al. ........... 623/1.39 |
| 2005/0181505 | A1 | | 8/2005 | Amir et al. |
| 2005/0196452 | A1 | * | 9/2005 | Boyan et al. ................... 424/486 |
| 2005/0246021 | A1 | * | 11/2005 | Ringeisen et al. ......... 623/17.11 |
| 2005/0272153 | A1 | * | 12/2005 | Xuenong et al. .............. 435/395 |
| 2006/0093646 | A1 | * | 5/2006 | Cima et al. .................... 424/425 |
| 2006/0105015 | A1 | | 5/2006 | Perla et al. |
| 2007/0104692 | A1 | * | 5/2007 | Quijano et al. .............. 424/93.7 |
| 2007/0104693 | A1 | * | 5/2007 | Quijano et al. .............. 424/93.7 |
| 2007/0104694 | A1 | * | 5/2007 | Quijano et al. .............. 424/93.7 |
| 2007/0104695 | A1 | * | 5/2007 | Quijano et al. .............. 424/93.7 |
| 2008/0097601 | A1 | * | 4/2008 | Codori-Hurff et al. ............ 623/8 |
| 2008/0300681 | A1 | * | 12/2008 | Rigotti et al. ..................... 623/8 |
| 2010/0161052 | A1 | * | 6/2010 | Rigotti et al. ..................... 623/8 |

OTHER PUBLICATIONS

International Search Report issued Sep. 22, 2008, in the related application PCT/US08/64745.

Supplementary European Search Report issued May 7, 2010, in the related application EP 08756226.0.

Kang et al, "Adipose Tissue Model Using Three-Dimensional Cultivation of Preadipocytes Seeded onto Fibrous Polymer Scaffolds," Tissue Engineering, 2005, pp. 458-468, vol. 11.

Moioli et al., "Matrices and Scaffolds for Drug Delivery in Dental, Oral, and Craniofacial Tissue Engineering," Advanced Drug Delivery Reviews, 2007, pp. 308-324, vol. 59.

Stosich et al., "Adipose Tissue Engineering From Human Adult Stem Cells: Clinical Implications in Plastic and Reconstructive Surgery," Plastic and Reconstructive Surgery, 2007, pp. 71-83, vol. 119.

Laschke et al., "Angiogenesis in Tissue Engineering: Breathing Life into Constructed Tissue Substitutes," Tissue Engineering, 2006, pp. 2093-2104, vol. 12.

Alhadlaq et al., "Engineered Adipose Tissue from Human Mesenchymal Stem Cells Maintains Predefined Shape and Dimension: Implications in Soft Tissue Augmentation and Reconstruction," Tissue Engineering, 2005, pp. 556-566, vol. 11.

Alhadlaq et al., Mesenchymal Stem Cells: Isolation and Therapeutics, Stem Cells Dev, 2004, pp. 436-448, vol. 13.

Alhadlaq et al., Adult Stem Cell Driven Genesis of Human-Shaped Articular Condyle, Ann Biomed Eng, 2004, pp. 911-923, vol. 32.

Alhadlaq et al., Tissue-engineered osteochondral constructs in the shape of an articular condyle, J Bone Joint Surg Am, 2005, pp. 936-944, vol. 87.

Alper, New insights into type 2 diabetes, Biomedicine, Science, 2000, pp. 37-39, vol. 289.

Arnez et al., Breast reconstruction using the free superficial inferior epigastric artery SIEA flap, Br J Plast Surg, 1999, pp. 276-279, vol. 52.

Arnez et al., Rational selection of flaps from the abdomen in breast reconstruction to reduce donor site morbidity, Br. J Plast. Surg, 1999, pp. 351-354, vol. 52.

Aust et al., Yield of human adipose-derived adult stem cells from liposuction aspirates, Cytotherapy, 2004, pp. 7-14, vol. 6, No. 1.

Brown et al., Breast implant adverse events during mammography: reports to the Food and Drug Administration, J Women's Health, 2004, pp. 371-378, vol. 13, No. 4.

Caplan et al., Mesenchymal stem cells: building blocks for molecular medicine in the 21st century, Trends Mol Med., 2001, pp. 259-264, vol. 7, No. 6.

Chajchir et al., Liposuction fat grafts in face wrinkles and hemifacial atrophy, Aesthetic Plast Surg, 1986, pp. 115-117, vol. 10.

De La Fuente et al., Fat injections for the correction of facial lipodystrophies: a preliminary report, Aesthetic Plast Surg, 1988, pp. 39-43, vol. 12.

European Communication dated May 10, 2011 in corresponding European Application No. EP 08756226.0, 4 pages.

European Communication dated Mar. 11, 2013 in corresponding European Application No. EP 08756226.0, 4 pages.

Flassbeck et al., Determination of siloxanes, silicon, and platinum in tissues of women with silicone gel-filled implants, Anal. Bioanal. Chem., 2003, pp. 356-362, vol. 375.

Goodwin et al., Complications in Smokers After Postmastectomy Tissue Expander/Implant Breast Reconstruction, Ann Plast Surg., 2005, pp. 16-19, vol. 55, No. 1.

Huang et al., Rat Extramedullary Adipose Tissue as a Source of Osteochondrogenic Progenitor Cells, Plast Reconstr Surg, 2002, pp. 1033-1041, vol. 109.

Jain et al., Dissecting Tumor Pathophysiology Using Intravital Microscopy, 2002, Nat. Rev. Cancer, pp. 266-276, vol. 2.

Jenkins et al., Breast Implants: Facts, Controversy, and Speculations for Future Research, J Invest Surg, 1996, pp. 1-12, vol. 9.

Lin et al. Multilineage differentiation of adipose-derived stromal cells from GFP transgenic mice, Mol Cell Biochem, 2006, pp. 69-78, vol. 285.

Marion et al., Mesenchymal Stem Cells and Tissue Engineering, Meth. Enzymol, 2006, pp. 339-361, vol. 420.

Matsudo et al., Experience of injected fat grafting, Aesthetic Plast Surg., 1988, pp. 35-38, vol. 12.

Mizuno et al., Simultaneous bilateral breast reconstruction with autologous tissue transfer after the removal of injectable artificial materials: a 12-year experience, Plast Reconstr Surg, 2005, vol. 116, pp. 450-458.

Moioli et al., Sustained Release of TGFβ3 from PLGA Microspheres and Its Effect on Early Osteogenic Differentiation of Human Mesenchymal Stem Cells, Tissue Eng, 2006, pp. 537-546, vol. 12, No. 3.

Niechajev et al., Long-Term Results of Fat Transplantation: Clinical and Histologic Studies, Plast Reconstr Surg, 1994, pp. 496-506, vol. 94, No. 3.

Ogawa et al. Adipogenic differentiation by adipose-derived stem cells harvested from GFP transgenic mice—including relationship of sex differences, Biochem. Biophys. Res Commun., 2004, pp. 511-517, vol. 319.

Ogawa et al. Osteogenic and chondrogenic differentiation by adipose-derived stem cells harvested from GFP transgenic mice, Biochem. Biophys. Res Commun., 2004, pp. 871-877, vol. 313.

(56) References Cited

OTHER PUBLICATIONS

Patrick et al., Long-Term Implantation of Preadipocyte-Seeded PLGA Scaffolds, Tissue Eng, 2002, pp. 283-293, vol. 8, No. 2.
Patrick, Breast tissue engineering, Annu. Rev. Biomed Eng, 2004, pp. 109-130, vol. 6.
Pittenger et al., Multilineage Potential of Adult Human Mesenchymal Stem Cells, Science, 1999, pp. 143-147, vol. 284.
Shenaq et al., New research in breast reconstruction: adipose tissue engineering, Clin Plast Surg, 2002, pp. 111-125, vol. 29, No. 1.
Shiffman, Silicone breast implant litigation Part 1, Med. Law, 1994, pp. 681-716, vol. 13.
Van Zele et al., Breast implants. A review. Acta Chir Belg, 2004, pp. 158-165, vol. 104.
Wong et al., Capsular Contracture in Subglandular Breast Augmentation with Textured versus Smooth Breast Implants: A Systematic Review, Plast Reconstr Surg, 2006, pp. 1224-1236, vol. 118, No. 5.
Yoshimura et al., Characterization of freshly isolated and cultured cells derived from the fatty and fluid portions of liposuction aspirates, J Cell Physiol, 2006, pp. 64-76, vol. 208.
Zheng et al., Mouse Adipose-Derived Stem Cells Undergo Multilineage Differentiation in Vitro but Primarily Osteogenic and Chondrogenic Differentiation in Vivo, Tissue Eng, 2006, pp. 1891-1901, vol. 12, No. 7.

\* cited by examiner

HYBRID SOFT TISSUE IMPLANTS FROM PROGENITOR CELLS AND BIOMATERIALS

CROSS-REFERENCE TO RELATED APPLICATIONS

The present application claims the benefit of PCT International Application No. PCT/US08/64745 filed 23 May 2008; which claims the benefit of U.S. Provisional Application No. 60/939,961, filed 24 May 2007; each of which is incorporated herein by reference in its entirety.

STATEMENT REGARDING FEDERALLY SPONSORED RESEARCH OR DEVELOPMENT

This invention was made with Government support under Grant EB006261 awarded by the National Institute of Biomedical Imaging and Bioengineering of the National Institutes of Health. The Government has certain rights in the invention.

FIELD OF THE INVENTION

The present invention generally relates to augmentation, repair, or regeneration of soft tissue.

BACKGROUND OF THE INVENTION

Soft tissue defects resulting from trauma, chronic diseases, congenital anomalies, aging or tumor resection often require implant technologies to restore the contour and symmetry of native tissue. For example, breast cancer patients suffer from loss of breast tissue after lumpectomy or mastectomy and are dependent on autologous tissue grafts or implant materials to restore the appearance of the breast mound. Adipose tissue engineering may provide an alternative by using progenitor cells, biomaterials, and bioactive molecules for the regeneration of biologically viable and remodeling-capable tissues for the repair of the breast contour and symmetry. But current synthetic or graft implant technologies suffer from common complications such as limited cell and tissue source, donor site morbidity, allergic reactions, foreign body reactions, rapid resorption and necrosis (see e.g., Flassbeck et al. (2003); Wong et al. (2006); Mizuno et al. (2005); Goodwin et al. (2005)).

Various autologous replacement or implant technologies have been previously developed. Autologous grafts have the advantage of using the patient's own tissue, and there is no need to test for allergic reaction. But autologous grafts and fillers may not be permanent, and volume reduction will occur over time. As with all procedures involving autologous tissue, donor site morbidity includes trauma and scarring. This is apparent in the reconstruction of larger defects, such as breast reconstruction for women after tumor resection. Furthermore, there may be a lack of appropriate donor site. For example, a very thin woman may not have the extra skin and adipose tissue in the abdomen or buttocks to act as donor tissue for breast reconstruction. Such patients can only be treated with artificial implants.

Breast implants have been used for many decades as prosthesis for augmentation, reconstruction (after mastectomy) or correction of the abnormalities that affect the shape and size of the breast (for review, see generally Van and Heymans (2004)). Approximately 300,000 women receive silicone breast implants every year in the United States alone, according to the American Society for Aesthetic Plastic Surgery (ASAPS) and The American Society of Plastic Surgeons (ASPS). The two primary types of synthetic breast implants are saline filled and silicone gel filled implants. Silicone implants have a silicone shell filled with viscous silicone gel whereas saline implants have a silicone elastomer shell filled with sterile saline liquid. Problems associated with synthetic breast implants include deflation, capsular contracture, infection, shifting, and calcium deposits. Other filler materials such as polyvinyl alcohol and hyaluronic acid have been introduced, however never progressed beyond experimental stages in the United States (Van and Heymans (2004)). Synthetic breast implants are typically not lifetime devices, and breast implantation is likely not a one-time surgery according to the Food and Drug Administration (FDA).

Mastectomy results in loss of the entire breast and reconstruction is necessary to restore natural body contour. The mainstay of non-autologous reconstruction involves the use of implants with or without skin expansion and autologous fat grafts (Alper (2000); Shenaq and Yuksel (2002)). However, recent advances made in synthetic and non-synthetic (autologous) approaches for breast mound reconstruction still yield suboptimal results. Current techniques for autologous breast reconstruction include the transverse rectus abdominis myocutaneous (TRAM) flap, and latissimus dorsi flap with or without alloplastic implants. Recently, free tissue transfer techniques have allowed the use of more sophisticated perforator flaps, which harvests skin and subcutaneous fat while sacrificing the underlying muscles. Examples include the deep inferior epigastric perforator (DIEP) flap and superior gluteal perforator flap (SGAP) (Arnez et al. (1999a, b)). But these procedures have significant limitations, including donor-site morbidity and limitations on the size of the reconstructed breasts. Moreover, autologous adipose tissue results in 50-70% graft volume reduction due to resorption (Niechajev and Sevcuk (1994); Matsudo and Toledo (1988); de la Fuente and Tavora (1988); Chajchir and Benzaquen (1986)). Balancing procedures such as augmentation, mastopexy (breast lift) or breast reduction are frequently necessary to restore symmetry.

Ideally, implant material should be easy to obtain, durable, non-immunogenic and biocompatible with the human body, easy to shape, able to be incorporated, and minimize donor site morbidity.

Thus there is the need for better implants that are durable, biocompatible, look and feel similar to natural breast tissue, and capable of maintaining shape and dimensions in the long term. Moreover, the implants should not obscure screening examinations and imaging studies in the detection of breast cancer (Brown et al. (2004)).

Soft tissue defects resulting from trauma, chronic diseases, congenital anomalies, aging or tumor resection often require implant technologies to restore the contour and symmetry of native tissue. Breast cancer patients suffer from loss of breast tissue after lumpectomy or mastectomy and are primarily dependent on implant materials to restore the appearance of the breast mound. Adipose tissue engineering provides tools including progenitor cells, biomaterials, and bioactive molecules for the regeneration of live, remodeling, bioactive tissues for the repair of the breast contour and symmetry.

Current technologies deliver synthetic materials that are foreign bodies such as silicone and saline implants. Autologous tissues are not used regularly due to lack of donor tissue, scarring, prolonged hospitalization, implant necrosis.

Current synthetic or graft implant technologies suffer from common complications such as limited cell and tissue source, donor site morbidity, allergic reactions, foreign body reactions, rapid resorption and necrosis.

Approximately 300,000 women receive silicone breast implants every year in the United States alone, according to the American Society for Aesthetic Plastic Surgery (ASAPS) and The American Society of Plastic Surgeons (ASPS), and breast surgical procedures costs add up to nearly $1.5 billion dollars a year. Recent enabling technologies using stem cells have shown the potential to revolutionize medical treatment including the methods of reconstruction of breast tissues post lumpectomy (partial removal of breast tissue) or mastectomy (complete resection of the breast). The present invention provides methods and compositions toward that goal.

SUMMARY OF THE INVENTION

The present application is directed to the use of mammalian cells and biocompatible materials for the development of soft tissue implants that circumvent common complications found with the use of conventional materials, such as silicone or saline based implants or autologous tissue grafts. Such complications include foreign body reaction, capsular contracture and leakage, as well as problems associated with autologous tissue grafts, such as donor site morbidity, lack of donor site, absorption, and necrosis. Furthermore, the present invention addresses problems with engineering volumes of adipose tissue in the scale of large soft tissue implants.

The application is directed to a hybrid soft tissue construct comprising a core material; a biomaterial matrix; and mammalian cells. In these constructs, the core material is acellular and biocompatible; the biomaterial matrix comprises the cells; the biomaterial matrix covers the acellular core; and the progenitor cells are capable of forming adipose cells.

The application is also directed to a method of augmenting or reconstructing a soft tissue of a mammal. The method comprises providing the above-described hybrid soft tissue construct; then implanting the engineered hybrid soft tissue construct into the mammal.

The application is further directed to a method of forming a hybrid soft tissue construct. The method comprises providing mammalian cells, a biomaterial matrix and a core material; contacting the mammalian cells and the biomaterial matrix; contacting the biomaterial matrix and the core material; and incubating the biomaterial matrix, the mammalian cells, and the core material to form an engineered hybrid soft tissue construct.

Additionally, the application is directed to the use of the above described construct for augmenting or reconstructing a soft tissue of a mammal.

Further, the application is directed to the use of the above described construct for the manufacture of a medicament for augmenting or reconstructing a soft tissue of a mammal.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A-B depict stem cells isolated from bone marrow biopsies or liposuction. FIG. 1C depicts stem cell differentiation into pre-adipocytes and adipocytes that regenerate adipose tissue. FIG. 1D depicts stem cell derived pre-adipocytes and adipocytes incorporated in pre-shaped engineered implants. Engineered adipose tissue can be fabricated to surround the acellular material core (artificial filler) of the implant. FIG. 1E depicts autologous implants being implanted back into the same patients, circumventing problems such as donor site morbidity, lack of donor site, and inflammation.

FIG. 2A shows bone marrow derived mesenchymal stem cells (hMSCs). FIG. 2B shows human adipose tissue derived MSCs. FIG. 2C shows adipogenic differentiation of hMSCs in culture for 4 wks and accumulation of intracellular lipids. FIG. 2D shows adipogenic differentiation in 3D hydrogel at 4 wks with formation of intracellular lipids. FIG. 2E shows hMSCs culture without differentiation stimulants for 4 wks. FIG. 2F shows hMSCs differentiated into adipocytes after 4 wks differentiation medium supplementation. FIG. 2G shows glycerol content of E and F showing adipogenic differentiation of hMSCs.

FIG. 3A-C depict isolation and expansion of human mesenchymal stem cells. FIG. 3D depicts hMSC seeding at varied concentrations in PEGDA hydrogel liquid solution. FIG. 3E depicts the acellular core of the hybrid implant. FIG. 3F depicts photopolymerization of the biomaterial matrix seeded with hMSCs. FIG. 3G depicts culturing of the resulting hybrid breast implant. FIG. 3H depicts implantation of the cultured hybrid breast implant into the dorsum of immunodeficient rats.

FIG. 4A represents the hybrid breast implant composed of a core of acellular biomaterial that provides the bulk volume, and the surrounding adipose tissue engineered from stem cells that coats and masks the breast implant. FIG. 4B represents a hybrid implant similar to that of FIG. 4A but with the addition of vascularization tunnels that induce host tissue infiltration for improved implant integration and formation of a vascular network.

DETAILED DESCRIPTION OF THE INVENTION

This present invention is directed to compositions and methods related to hybrid soft tissue implants. The implant is a construct comprising a core material; a biomaterial matrix; and mammalian cells. In these constructs, the core material is acellular and biocompatible; the biomaterial matrix comprises the cells; and the biomaterial matrix covers the acellular core.

The hybrid soft tissue implants of the present invention can be used for augmentation and reconstruction of any soft tissue. Augmentation and/or reconstruction can be required due to, for example, trauma, congenital anomalies, tumor resection, and/or other diseases. Several examples of the application of hybrid soft tissue implants include breast implant, facial implants, and soft tissue implants elsewhere in the human body such as after burns and trauma. Preferably, the hybrid soft tissue implant is a hybrid soft tissue breast implant.

By using an inner core of artificial biocompatible acellular material, the hybrid implant reduces the challenges for engineering the volume of engineered live adipose tissue necessary for implant fabrication, thus reducing volume reduction, resorption and necrosis. As such, the hybrid soft tissue implants described herein can be of a larger volume than currently available biological implants. Furthermore, the outer layer of adipose tissue (and/or adipose progenitor cells) can mask the foreign portion of the implant from the host, thereby improving incorporation and long-term survival and preventing complications associated with allergic reactions and/or foreign body reactions.

The application is also directed to a method of forming method of forming a hybrid soft tissue construct. The method comprises providing mammalian cells, a biomaterial matrix and a core material; contacting the mammalian cells and the biomaterial matrix; contacting the biomaterial matrix and the core material; and incubating the biomaterial matrix, the progenitor cells, and the core material to form an engineered hybrid soft tissue construct.

Thus the hybrid soft tissue implants and methods for their production and use described herein can circumvent issues associated with previous implant options using an adipose cell layer (arising from progenitor cells) in a biomaterial matrix surrounding a synthetic biocompatible core to fabricate a hybrid soft tissue implant that is host friendly, minimizes donor site morbidity, allergic reactions, foreign body reactions, rapid resorption, and necrosis, and relies on an abundant progenitor cell source.

Figure 1:
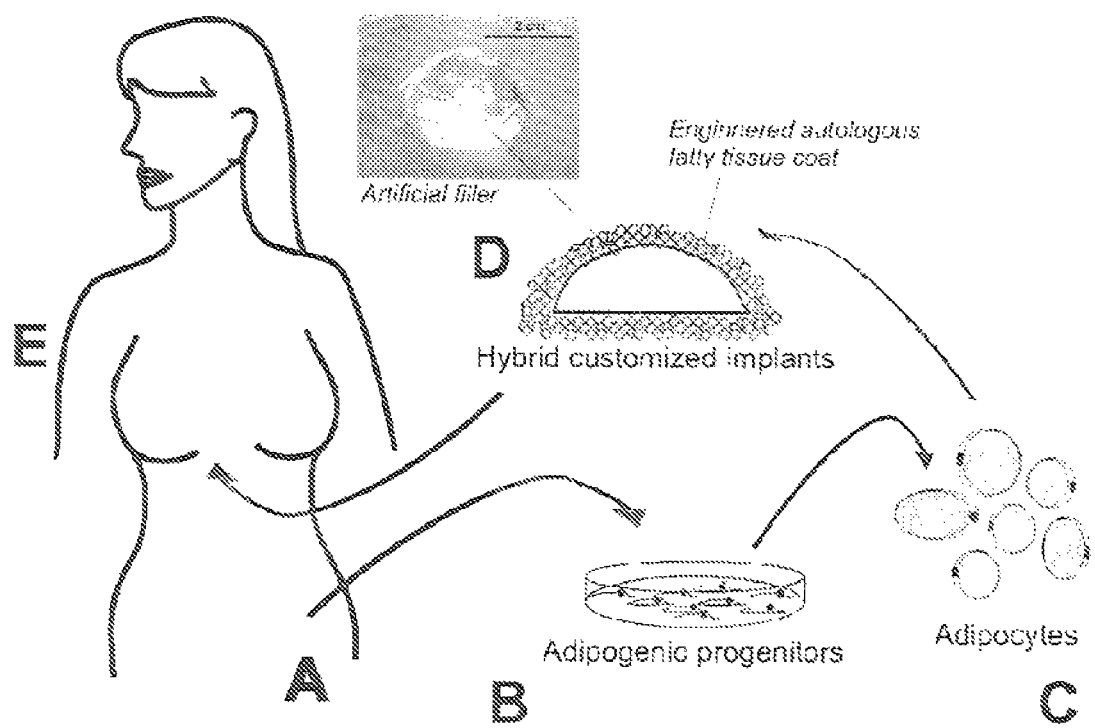
FIG. 1 is a diagram depicting autologous stem cell based tissue engineering.

The present invention utilizes principles of tissue engineering to combine progenitor cells capable of forming adipose tissue and biomaterials so as to provide bioactive, better incorporated, longer-lasting, and live engineered implants for reconstructive and regenerative procedures (see e.g., FIG. 1). Such an approach can supplant current inert and limited reconstructive soft tissue fillers.

Mammalian Cells

Preferably, the mammalian cells are, or are capable of forming, adipose cells, interstitial cells, endothelial cells or smooth muscle cells, or a combination thereof. More preferably, the mammalian cells are progenitor cells, adipose cells, or a combination thereof. Even more preferably, the mammalian cells are progenitor cells capable of forming adipose cells. Most preferably, the progenitor cells are adipose progenitor cells. Here, the adipose progenitor cells are preferably adipose tissue derived cells, pre-adipocytes, mesenchymal stem cells (MSC), MSC-derived cells, or adipocytes.

As an example, adipose progenitor cells can be selected from adipose tissue-derived cells, pre-adipocytes, mesenchymal stem cells (MSC), bone marrow, MSC-derived cells such as MSC-derived adipogenic cells, adipocytes, or other similar progenitor cells that can give rise to adipose cells. The utilization of adipogenic progenitors such as stem cells can circumvent limitations of cell source as these cells are readily harvested, expanded, and differentiated into adipogenic cells.

Native adipose tissue is supported by a network of fibrous tissues. Not surprisingly, engineered adipose tissue can require similar structural support in the form of biomaterial scaffold or possibly by invasion of recruited host cells forming reinforcing networks. Adipose tissue implant survival can also be regulated by the availability of progenitors, such as pre-adipocytes, for maintenance and repair upon remodeling or injury. Mature adipocytes do not proliferate. Thus, the adipocyte precursor, or pre-adipocyte, that can be derived from cells such as mesenchymal stem cells plays a role in native as well as engineered adipose tissue regeneration due to its proliferation and differentiation potential. Tissue engineering approaches described herein can provide the progenitor cell populations and integrative architectures necessary for long-term maintenance of engineered adipose tissue.

Progenitor cells can be isolated, purified, and/or cultured by a variety of means (see e.g., Example 2). Methods for the isolation and culture of progenitor cells are discussed in, for example, Marion and Mao (2006). The progenitor cells can be derived from the same or different species as the transplant recipient. For example, the progenitor cells can be derived from an animal, including, but not limited to, mammals, reptiles, and avians, more preferably horses, cows, dogs, cats, sheep, pigs, and chickens, and most preferably human. The progenitor cells can be cells or tissues transplanted from a different individual are referred to as allogeneic or autologous. Preferably, the progenitor cells are autologous (i.e., reimplanted in the same individual as they come from). Allogeneic cells may also be used with or without post-surgical administration of immunosuppresants.

Progenitor cells infused into the matrix biomaterial and then coated over the acellular core material are usually a progenitor cell capable of differentiating into or otherwise forming adipose tissue. For example, the tissue progenitor cell can be a mesenchymal stem cell (MSC), preferably a human MSC. MSCs are generally capable of differentiating into adipocytes, as well as other cells known in the art. The adipose progenitor cell can be substantially undifferentiated. For example, the adipose progenitor cell can be freshly isolated and not pre-treated with growth factors before being introduced into the matrix.

In various embodiments, progenitor cells can be differentiated and form adipose tissue for use in breast reconstruction (see e.g., FIG. 1). Populations of progenitors and pre-adipocytes can be isolated from, for example, liposuction aspirates and show high expandability in vitro (Yoshimura et al. (2006); Aust et al. (2004)). The same adipose progenitors that differentiate into mature adipocytes have the potential to differentiate into other cellular phenotypes such as osteoblasts and chondrocytes (Huang et al. (2002); Ogawa et al., 2004a, b; Zheng et al. (2006); Lin et al. (2006)). Mesenchymal stem cells (MSCs) isolated from bone marrow can also undergo multiple population doublings and differentiate into adipocytes, fibroblasts, osteoblasts, chondrocytes, tenocytes and myocytes (Caplan and Bruder (2001); Pittenger et al. (1999); Alhadlaq and Mao (2004)).

Progenitor cells can be present in the biomaterial matrix at various amounts. Density-dependent inhibition of cell division (previously termed contact inhibition) can be a factor in cell survival, for example when mesenchymal stem cells give rise to adipogenic progenitor cells and end-stage adipose cells in development. Too many cells seeded in an engineered tissue may create shortage of locally available mitogens, growth factors and/or survival factors, potentially leading to apoptosis and causing unnecessary waste of in vitro cell expansion time. On the other hand, too few cells seeded in an engineered tissue may lead to poor regeneration outcome. Various methodologies for optimizing the density of tissue progenitor cells so as to maximize the regenerative outcome of hybrid soft tissue implant are known to the art. Various matrix seeding densities can be monitored over time and at end-point cell densities with, for example, histology, structural analysis, immunohistochemistry, biochemical analysis, and mechanical properties. As will be recognized by one skilled in the art, the seeded cell densities of progenitor cells can vary according to, for example, progenitor type, tissue type, matrix material, matrix volume, infusion method, seeding pattern, culture medium, growth factors, incubation time, incubation conditions, and the like. Generally, the tissue progenitor cells can be present in the matrix material at a density of about $0.0001 \times 10^6$ cells ml$^{-1}$ to about $1000 \times 10^6$ cells ml$^{-1}$, preferably about $0.5 \times 10^6$ cells ml$^{-1}$ to $100 \times 10^6$ cells ml$^{-1}$. For example, the tissue progenitor cells and/or the vascular progenitor cells can be present in the matrix material at a density of about $1 \times 10^6$ cells ml$^{-1}$, $5 \times 10^6$ cells ml$^{-1}$, $10 \times 10^6$ cells ml$^{-1}$, $15 \times 10^6$ cells ml$^{-1}$, $20 \times 10^6$ cells ml$^{-1}$, $25 \times 10^6$ cells ml$^{-1}$, $30 \times 10^6$ cells ml$^{-1}$, $35 \times 10^6$ cells ml$^{-1}$, $40 \times 10^6$ cells ml$^{-1}$, $45 \times 10^6$ cells ml$^{-1}$, $50 \times 10^6$ cells ml$^{-1}$, $55 \times 10^6$ cells ml$^{-1}$, $60 \times 10^6$ cells ml$^{-1}$, $65 \times 10^6$ cells ml$^{-1}$, $70 \times 10^6$ cells ml$^{-1}$, $75'10^6$ cells ml$^{-1}$, $80 \times 10^6$ cells ml$^{-1}$, $85 \times 10^6$ cells ml$^{-1}$, $90 \times 10^6$ cells ml$^{-1}$, $95 \times 10^6$ cells ml$^{-1}$, or $100 \times 10^6$ cells ml$^{-1}$.

In some embodiments, the progenitor cells used to seed the matrix are transformed with a heterologous nucleic acid so as to express a bioactive molecule, or heterologous protein or to overexpress an endogenous protein. As an example, the progenitor cells to be seeded in the matrix can be genetically modified to expresses a fluorescent protein marker. Exemplary markers include GFP, EGFP, BFP, CFP, YFP, and RFP. As another example, progenitor cells to be seeded in the matrix can be genetically modified to express an angiogenesis-related factor, such as activin A, adrenomedullin, aFGF, ALK1, ALK5, ANF, angiogenin, angiopoietin-1, angiopoietin-2, angiopoietin-3, angiopoietin-4, angiostatin, angiotropin, angiotensin-2, AtT20-ECGF, betacellulin, bFGF, B61, bFGF inducing activity, cadherins, CAM-RF, cGMP analogs, ChDI, CLAF, claudins, collagen, collagen receptors $\alpha.sub.1\beta.sub.1$ and $\alpha.sub.2\beta.sub.1$, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation sphingolipid G-protein coupled receptor-1 (EDG1), ephrins, Epo, HGF, TNF-alpha, TGF-beta, PD-ECGF, PDGF, IGF, IL8, growth hormone, fibrin fragment E, FGF-5, fibronectin and fibronectin receptor $\alpha5\beta1$, Factor X, HB-EGF, HBNF, HGF, HUAF, heart derived inhibitor of vascular cell proliferation, IFN-$\gamma$, ILL IGF-2, integrin receptors, K-FGF, LIF, leiomyoma-derived growth factor, MCP-1, macrophage-derived growth factor, monocyte-derived growth factor, MD-ECI, MECIF, MMP 2, MMP3, MMP9, urokiase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-$\beta$, PD-ECGF, PAI-2, PD-ECGF, PF4, P1GF, PKR1, PKR2, PPAR$\gamma$, PPAR$\gamma$ ligands, phosphodiesterase, prolactin, prostacyclin, protein S, smooth muscle cell-derived growth factor, smooth muscle cell-derived migration factor, sphingosine-1-phosphate-1 (S1P1), Syk, SLP76, tachykinins, TGF-beta, Tie 1, Tie2, TGF-$\beta$, and TGF-$\beta$ receptors, TIMPs, TNF-$\alpha$, TNF-$\oplus$, transferrin, thrombospondin, urokinase, VEGF-A, VEGF-B, VEGF-C, VEGF-D, VEGF-E, VEGF, VEGF.sub.164, VEGI, EG-VEGF, VEGF receptors, PF4, 16 kDa fragment of prolactin, prostaglandins E1 and E2, steroids, heparin, 1-butyryl glycerol (monobutyrin), and/or nicotinic amide. As another example, progenitor cells to be seeded in the matrix can be transfected with genetic sequences that are capable of reducing or eliminating an immune response in the host (e.g., expression of cell surface antigens such as class I and class II histocompatibility antigens may be suppressed). This may allow the transplanted cells to have reduced chance of rejection by the host.

In some embodiments, the matrix material can be seeded with one or more cell types in addition to the first tissue progenitor cell. Such additional cell types can include (but are not limited to) skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, osteoclasts, or chondrocytes. These cell-types may be introduced prior to, during, or after coating of the acellular core material with the cell-seeded matrix. Such introduction may take place in vitro or in vivo. When the cells are introduced in vivo, the introduction may be at the site of the engineered vascularized tissue or at a site removed therefrom. Exemplary routes of administration of the cells include injection and surgical implantation.

Core and Matrix

The present invention utilizes a biomaterial matrix in the formation of hybrid soft tissue implants. The various approaches outlined herein provide a technique for breast implant functionalization by fabricating a layer of adipose tissue from progenitor cells (e.g., stem cells) seeded in biomaterial matrix to surround an acellular artificial biocompatible core that provides the bulk of the implant. The core of the hybrid soft tissue implant can be composed of a biocompatible material onto which progenitor cells are coated so as to form a hybrid soft tissue implant with an inert layer (i.e., inner core) and a living tissue layer (i.e., outer adipose tissue layer). Further, the progenitor cells can be seeded in or on a biomaterial matrix which is then coated on the core biomaterial.

Core Acellular Biocompatible Material

Various embodiments of the present invention utilize an acellular core of biocompatible material in the fabrication of a hybrid soft tissue implants.

Current artificial breast implants are recognized as foreign bodies upon implantation and develop side effects, including capsular contracture and change in morphology and softness, leading to the potential need for implant removal. According to the approaches described herein, a core acellular biocompatible material, which can form the bulk of the implant, is surrounded by an adipose cellular layer formed from adipogenic progenitor cells. Such an adipose cellular layer can serve to mask the core acellular biocompatible material from recognition by the host as a foreign body.

The acellular core of the hybrid soft tissue implant can be, for example, any artificial implant material currently used for breast implantation suitable to be functionalized by surrounding autologous engineered adipose tissue from progenitor cells. For the example, the acellular core can be a conventional saline or silicone gel implant, including multiple lumen designs, so-called "gummy bear" or solid, high-cohesive, form-stable implants, or adaptations of such. The shells of conventional implants are made of materials that include, for example, silicone elastomer. It is also understood that the core may be coated with a material such as elastomer or polyurethane foam as used in conventional breast implant materials.

The acellular core of the hybrid soft tissue implant can be a polyethylene glycol diacrylate (PEGDA) hydrogel.

The acellular core material can make up the bulk of the implant. One skilled in the art will be able to determine the volume and geometry of the acellular core based, at least in part, upon the needs of the subject. The acellular core can be, for example, as small as about $0.5\ cm^3$ to as large as about $100\ cm^3$. For example, the volume of the acellular core of the hybrid soft tissue implant can be about $5\ cm^3$, about $10\ cm^3$, about $20\ cm^3$, about $30\ cm^3$, about $40\ cm^3$, or about 50 cm.

Matrix Biomaterials

Various embodiments of the present invention employ a core acellular biocompatible material onto which progenitor cells seeded in a biomaterial matrix are coated so as to form a hybrid soft tissue implant. Such matrix biomaterials can: allow cell attachment and migration; deliver and retain cells and biochemical factors; enable diffusion of cell nutrients and expressed products; and/or exert certain mechanical and biological influences to modify the behavior of the cell phase. The matrix is generally a porous, microcellular scaffold of a biocompatible material that provides a physical support and an adhesive substrate for seeding progenitor cells during in vitro culturing and subsequent in vivo implantation.

A matrix with a high porosity and an adequate pore size is preferred so as to facilitate cell seeding and diffusion throughout the cellular layer of the hybrid soft tissue implant of both cells and nutrients. Matrix biodegradability is also preferred. The rate at which degradation occurs should coincide as much as possible with the rate of adipose tissue formation. Thus, while adipose cells are fabricating their own natural structure around themselves, the matrix is able to provide structural integrity and eventually break down leaving the adipose tissue layer surrounding the acellular core of the hybrid soft tissue implant. Suitable matrix materials are discussed in, for example, Ma and Elisseeff, ed. (2005); Saltzman (2004).

The matrix configuration is preferably a pliable, biocompatible, porous template that allows for adipose tissue growth. The porosity of the matrix is a design parameter that influences cell seeding and/or cell infiltration. The matrix can be designed to incorporate extracellular matrix proteins that influence cell adhesion and migration in the matrix.

This allows for the cell-seeded matrix to be coated on the acellular core in a substantially liquid phase, after which the matrix can be transitioned to the substantially gelled phase. The transition between phases can be stimulated by a variety of factors including, but limited to light, temperature, chemical, magnetic, electrical, and mechanical stimulus. Preferably, the liquid phase of the matrix has a lower viscosity that provides for optimal distribution of progenitor cells and uniform coating of the acellular core material, while the solid phase of the matrix has an elevated viscosity that provides for seeded matrix retention on acellular core material and/or at or within the target tissue. The solid phase of the matrix should have an adequate porosity and an adequate pore size so as to facilitate cell seeding and diffusion throughout the whole cellular layer structure of both cells and nutrients.

As an example, a suitable matrix material for use in the present invention is a polymeric hydrogel such as a PEGDA hydrogel liquid solution that photopolymerizes.

The biomaterial matrix can be formed of synthetic polymers. Such synthetic polymers include, but are not limited to, polyurethanes, polyorthoesters, polyvinyl alcohol, polyamides, polycarbonates, polyvinyl pyrrolidone, marine adhesive proteins, cyanoacrylates, analogs, mixtures, combinations and derivatives of the above. Alternatively, the matrix can be formed of naturally occurring biopolymers. Such naturally occurring biopolymers include, but are not limited to, fibrin, fibrinogen, fibronectin, collagen, and other suitable biopolymers. Also, the matrix can be formed from a mixture of naturally occurring biopolymers and synthetic polymers.

The matrix material the matrix can include, for example, a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g. alginate), polyphosphazene, or polyacrylate, or a polyethylene oxide-polypropylene glycol block copolymer. Matrices can be produced from proteins (e.g. extracellular matrix proteins such as fibrin, collagen, and fibronectin), polymers (e.g., polyvinylpyrrolidone), or hyaluronic acid. Synthetic polymers can also be used, including bioerodible polymers (e.g., poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, poly(vinylimidazole), chlorosulphonated polyolifins, polyethylene oxide, polyvinyl alcohol, Teflon®, and nylon.

In various embodiments, adipose progenitor cells are introduced (e.g., infused or seeded) into the substantially liquid phase of the matrix capable of forming a gelled phase matrix. The adipose progenitor cells can be introduced in a homogenous or heterogeneous distribution throughout the liquid. It is contemplated that more than one type of progenitor cell can be introduced into the matrix. For example, different types of adipose progenitor cells can be introduced into the matrix. As another example, adipose progenitor cells can be introduced into the matrix along with vascular progenitor cells.

The matrix can also include one or more of enzymes, ions, growth factors, and/or biologic agents. For example, the matrix can contain a growth factor (e.g., and angiogenic growth factor, or tissue specific growth factor). Such a growth factor can be supplied at a concentration of about 0 to 1000 ng/mL. For example, the growth factor can be present at a concentration of about 100 to 700 ng/mL, at a concentration of about 200 to 400 ng/mL, or at a concentration of about 250 ng/mL.

PEGDA has been well characterized and can support adipogenic differentiation of stem cells and adipose tissue regeneration in vitro and in vivo while maintaining shape and dimensions. A PEGDA hydrogel core material is biocompatible and induces minimal immune response.

Crosslinking of the biocompatible matrix material can help prevent collapse of an implant even where a portion is resected. For example, one could remove a large slice from a circular shaped hydrogel, and the implant can retain the remaining shape, allowing for stability and future localized repair. This provides an advantage in patients with susceptibility for tumor recurrence, allowing for lumpectomy, or other similar process, to be performed without compromising structural integrity of the remaining breast tissue/implant.

The choice of biomaterial scaffold can impact the long term survival of the engineered adipose tissue. Using different scaffolding materials, seeding rat pre-adipocytes in biodegradable poly-lactic-co-glycolic acid (PLGA) scaffolds, resulted in subsequent resorption of the engineered adipose tissue (Patrick (2004); Patrick et al. (2002)). Interestingly, absence of adipose tissue corresponded with absence of the PLGA scaffold due to degradation, suggesting dependence of the new adipose tissue for a continued support structure. Native adipose tissue is supported by a network of fibrous tissues. Engineered adipose tissue can require similar structural support in the form of biomaterial scaffold or possibly by invasion of recruited host cells forming reinforcing networks.

Tissue Functions

The hybrid soft tissue implant can be used as an implant in any situation where a soft tissue implant is desired, including but not limited to applications for the breast, face or hand. The implant can mimic all natural functions of the target tissue or a portion thereof. When regenerating or repairing complex tissues and organs that include multiple cellular phenotypes as well as numerous structures and functions, tissue engineering design does not necessarily need to include parameters for complete regeneration. The tissue engineering design can focus on selected functions and structures. Replicating all functions completely may entail larger inputs of effort and time, might be impractical, and, at times, unnecessary. For example, the soft tissue of the hybrid implant can exclude components of the target tissue that may lead to the development of disease. As such, efforts can be directed towards the neoformation of healthy engineered tissue with decreased susceptibility for recurrence of disease. The mammalian breast provides an example of functionally selective engineered tissues. The engineered mammalian breast substitutes can exclude some components of the original tissue, such as the mammary glands, while still fulfilling reconstruction requirements by replacing it with fatty tissue in the form of a breast. Restoration of glandular tissue in a patient with a history of breast cancer implicates the potential for cancer recurrence and thus could be contraindicated. In most cases, there is little motivation and/or need for glandular regeneration after breast resection; thus its exclusion during breast tissue engineering design can lead to a greater resistance to recurring tumors post-reconstruction.

Likewise, breast augmentation procedures are achieved with placement of synthetic implants, which are foreign materials and recognized as such. The body normally reacts by forming a fibrous capsule to "seal off" this foreign body. Capsular contracture is universal and severe contractures can lead to pain, discomfort, and deformation of the breast. Treatment includes removal or replacement of the implant, and secondary procedures such as capsulotomy or capsulectomy (Shiffman (1994); Jenkins et al. (1996)). The hybrid implant approach described herein, coating an acellular core material with an adipose tissue layer, can serve to shield the core from recognition as a foreign material, and so, reduce or eliminate complications such as capsular contracture.

Given the current reservations in incorporating glandular tissues as design parameters in breast tissue engineering, and the need for preventing capsular contracture, adipose tissue is well suited for breast augmentation or reconstruction as a filler material.

Vascularization

Long-term survival of engineered adipose tissue can depend on adequate vascularization, structural support, and availability of progenitors. Long-term loss of engineered adipose tissue, similar to resorption of autologous fat grafts, may result from suboptimal vascularization. The hybrid implant approach described herein, an acellular core forming the bulk of the implant, coated with an adipose tissue layer provides for increased implant volume while reducing suboptimal vascularization by way of reducing the amount of engineered tissue to be vascularized. By providing a thinner layer of living tissue, the vascularization process can become more efficient.

Recruitment or delivery of angiogenic cells to engineered adipose tissue is one parameter in engineering design for achieving the minimal longevity requirements of implanted reconstructive tissues. Additionally, long-term loss of engineered adipose tissue, similar to absorption of autologous fat grafts, may result from suboptimal vascularization. Hence, recruitment or delivery of angiogenic cells to engineered adipose tissue can be included as a parameter in engineering design for achieving minimal longevity requirements of implanted reconstructive tissues.

In various embodiments, vascular progenitor cells can be seeded in the biomaterial matrix along with adipose progenitor cells, so as to facilitate vascular formation. Vascular progenitor cells are progenitor cells capable of differentiating into or otherwise forming vascular cells. Vascular progenitor cells include, for example, hematopoietic stem cells (HSC), HSC-derived endothelial cells, blood vascular endothelial cells, lymph vascular endothelial cells, endothelial cell lines, primary culture endothelial cells, endothelial cells derived from stem cells, bone marrow derived stem cells, cord blood derived cells, human umbilical vein endothelial cells (HUVEC), lymphatic endothelial cells, endothelial progenitor cells, and stem cells that differentiate into endothelial cells, endothelial cell lines, endothelial cells generated from stem cells in vitro, endothelial cells from adipose tissue, smooth muscle cells, interstitial fibroblasts, myofibroblasts, periodontal tissue or tooth pulp, and vascular derived cells, or other similar progenitor cells that can give rise to vascular cells.

Methods for measuring angiogenesis in engineered tissue are standard in the art (see e.g., Jain et al. (2002) Nat. Rev. Cancer 2:266-276; Ferrara, ed. (2006) Angiogenesis, CRC, ISBN 0849328446). During early blood vessel formation, immature vessels resemble the vascular plexus during development, by having relatively large diameters and lacking morphological vessel differentiation. Over time, the mesh-like pattern of immature angiogenic vessels gradually mature into functional microcirculatory units, which develop into a dense capillary network having differentiated arterioles and venules. Angiogenesis can be assayed, for example, by measuring the number of non-branching blood vessel segments (number of segments per unit area), the functional vascular density (total length of perfused blood vessel per unit area), the vessel diameter, or the vessel volume density (total of calculated blood vessel volume based on length and diameter of each segment per unit area).

The compositions of the invention generally have increased vascularization as compared to soft tissue implants produced according to conventional means. For example, blood vessel formation (e.g., angiogenesis, vasculogenesis, formation of an immature blood vessel network, blood vessel remodeling, blood vessel stabilization, blood vessel maturation, blood vessel differentiation, or establishment of a functional blood vessel network) in the engineered tissue or organ can be increased by at least 5%, 10%, 20%, 25%, 30%, 40%, or 50%, 60%, 70%, 80%, 90%, or even by as much as 100%, 150%, or 200% compared to a corresponding engineered tissue or organ that is not formed by methods described herein. The vascularization of the engineered tissue is preferably a stable network of blood vessels that endures for at least 1 day, 2 days, 3 days, 4 days, 5 days, 6 days, 1 week, 2 weeks, 3 weeks, 1 month, 2 months, 3 months, 4 months, 5 months, 6 months, or even 12 months or more. Preferably, the vascular network of the engineered tissue is integrated into the circulatory system of the tissue, organ, or subject upon introduction thereto.

Coating And Culturing

To form the hybrid soft tissue implants described herein, adipose progenitor cells are introduced (e.g., coated, implanted, injected, infused, or seeded) into or onto an artificial structure (e.g., a scaffold comprising a matrix material) capable of coating the acellular core material of the hybrid implant. It is contemplated that more than one type of adipose progenitor cell can be introduced into the matrix. Similarly, it is contemplated that more than one type of vascular progenitor cell can be introduced into the matrix.

Tissue progenitor cells and/or vascular progenitor cells can be introduced into or onto the biomaterial matrix by a variety of means known to the art (see e.g., Example 3). Methods for the infusion, or seeding, of progenitor cells into or into the matrix material are discussed in, for example, Ma and Elisseeff, ed. (2005), Saltzman (2004) and Minuth et al. (2005). Methods of addition of additional agents vary, as discussed below.

Methods of culturing and differentiating seeded progenitor cells in or on biomaterials are generally known in the art (see e.g., Saltzman (2004); Vunjak-Novakovic and Freshney, eds. (2006); Minuth et al. (2005)). As will be appreciated by one skilled in the art, the time between coating the progenitor cell formulation onto the core biomaterial and engrafting the hybrid soft tissue implant can vary according to particular application. Incubation (and subsequent replication and/or differentiation) of the engineered composition containing progenitor cells on the core biomaterial can be, for example, at least in part in vitro, substantially in vitro, at least in part in vivo, or substantially in vivo. Determination of optimal culture time is within the skill of the art. A suitable medium can be used for in vitro progenitor cell infusion, differentiation, or cell transdifferentiation (see e.g., Vunjak-Novakovic and Freshney, eds. (2006); Minuth et al. (2005)). The culture time can vary from about an hour, several hours, a day, several days, a week, or several weeks. The quantity and type of cells present in the matrix can be characterized by, for example, morphology by ELISA, by protein assays, by genetic assays, by mechanical analysis, by RT-PCR, and/or by immunostaining to screen for cell-type-specific markers (see e.g., Minuth et al. (2005)).

Preferably, the core acellular material is immersed in a progenitor cell seeded solution. For example, a hydrogel core implant can be submerged in a hydrogel liquid solution seeded with human mesenchymal stem cells, after which the adhering seeded hydrogel liquid can be photopolymerized to surround the artificial core (see e.g., Example 2).

Volume Maintenance

A major problem associated with engineered adipogenesis for breast tissue engineering is eventual resorption and necrosis resulting in significant changes in appearance. Loss of engineered adipose tissue is generally attributed to lack of blood supply, integration with the host, and inadequate degradation properties of the scaffolding biomaterial, which results in the lack of a support structure. Native breast adipose tissue is well vascularized and contains fibrous tissue supporting structures, the suspensory ligaments. Not surprisingly, engineered adipose tissue requires similar structural support in the form of biomaterial scaffold or possibly by invasion of recruited host cells forming reinforcing networks.

The approaches described herein provide for size and shape retention of engineered tissue implants. Size and shape retention can be an important factor in adipose tissue engineering given aesthetic and other requirements involved with breast reconstruction and augmentation. By providing an acellular core, which can make up the bulk of a hybrid implant, the tissue implant can better retain size and shape and, as discussed above, increased vascularization of the living adipose tissue layer.

Channels

Lack of vascularization is thought to cause, at least in part, adipose tissue resorption and necrosis.

Thus, the matrix can contain one or more physical channels. Such physical channels include microchannels and macrochannels. Microchannels generally have an average diameter of about 0.1 μm to about 1,000 μm. Microchannels are typically a naturally occurring feature of certain matrix materials.

Matrix macrochannels can accelerate angiogenesis and bone or adipose tissue formation, as well as direct the development of vascularization and host cell invasion. Macrochannels can be a naturally occurring feature of certain matrix materials and/or specifically engineered in the matrix material. Formation of macrochannels can be according to, for example, mechanical and/or chemical means (see e.g., Example 3).

Figure 4:
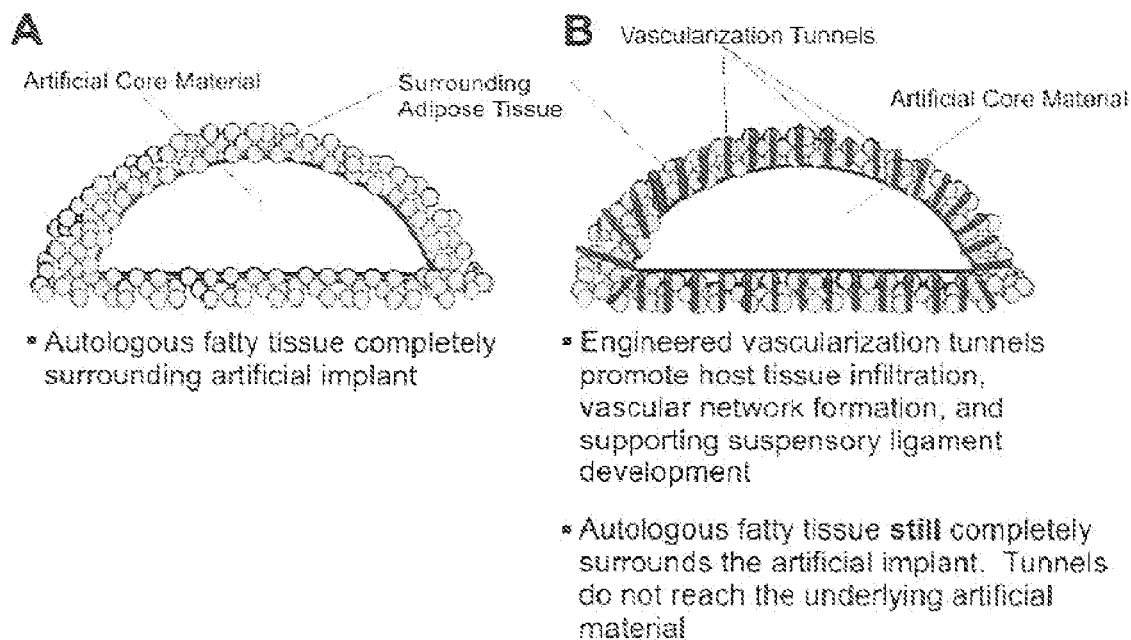
FIG. 4 is diagrams illustrating cross section of various embodiments of hybrid soft tissue implant.

To provide for enhanced vascularization, the matrix portion of the construct can be engineered to contain macrochannels. Hydrogel constructs with engineered macrochannels implanted in vivo induce host tissue infiltration with vascular characteristics (FIG. 4). Thus, tunnels, or similar structures, can be fabricated in the engineered adipose tissue surrounding the artificial implant (Example 3). This approach provides a hybrid implant technique that can, at least in part, circumvent fat tissue resorption post-implantation through selection of suitable scaffolding biomaterials with pre-designed architecture for engineered adipose tissue formation. Circumvention of fat tissue resorption post-implantation can also be accomplished, at least in part, by minimizing the amount of live tissue required in the breast implant, using an artificial acellular material as the core of the implant that provides enough bulk for restoration of large contours and symmetry. Of course, the scaffolding biomaterials architecture (e.g., macrochannels) and minimization of the amount of live tissue can be used in conjunction to further reduce fat tissue resorption post-implantation.

Macrochannels can extend variable depths through the matrix biomaterial in which progenitor cells are seeded. Preferably the macrochannel does not extend so far as to expose the acellular core material to the host. Macrochannels can be a variety of diameters. Generally, the diameter of the macrochannel will be chosen according to increased optimization of vascularization of the cellular layer of the hybrid soft tissue implant. As described above, methods for measuring angiogenesis in engineered tissue are standard in the art (Jain et al. (2002); Ferrara, ed. (2006)). The macrochannels can have an average diameter of, for example, about 0.1 mm to about 50 mm. For example, macrochannels can have an average diameter of about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, about 10 mm, about 15 mm, about 20 mm, about 25 mm, about 30 mm, about 35 mm, about 40 mm, or about 45 mm. On skilled in the art will understand that the distribution of macrochannel diameters can be a normal distribution of diameters or a non-normal distribution diameters.

Added Drugs and/or Diagnostics

In some embodiments, the methods and compositions of the invention further comprise additional agents introduced into or onto the matrix along with the progenitor cells. Various agents that can be introduced include, but are not limited to, bioactive molecules, biologic drugs, diagnostic agents, and/or strengthening agents.

The matrix can further comprise a bioactive molecule. The cells of the matrix can be, for example, genetically engineered to express the bioactive molecule or the bioactive molecule can be added to the matrix. The matrix can also be cultured in the presence of the bioactive molecule. The bioactive molecule can be added prior to, during, or after contacting the matrix with the progenitor cells. Non-limiting examples of bioactive molecules include activin A, adrenomedullin, aFGF, ALK1, ALK5, ANF, angiogenin, angiopoietin-1, angiopoietin-2, angiopoietin-3, angiopoietin-4, angiostatin, angiotropin, angiotensin-2, AtT20-ECGF, betacellulin, bFGF, B61, bFGF inducing activity, cadherins, CAM-RF, cGMP analogs, ChDI, CLAF, claudins, collagen, collagen receptors $\alpha_1\beta_1$ and $\alpha_2\beta_1$, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation sphingolipid G-protein coupled receptor-1 (EDG1), ephrins, Epo, HGF, PD-ECGF, PDGF, IGF, IL8, growth hormone, fibrin fragment E, FGF-5, fibronectin, fibronectin receptor $\alpha_5\beta_1$, Factor X, HB-EGF, HBNF, HGF, HUAF, heart derived inhibitor of vascular cell proliferation, IFN-$\gamma$, ILL IGF-2, integrin receptors (e.g., various combinations of a subunits (e.g., $\alpha_1$, $\alpha_2$, $\alpha_3$, $\alpha_4$, $\alpha_5$, $\alpha_6$, $\alpha_7$, $\alpha_8$, $\alpha_9$, $\alpha_E$, $\alpha_V$, $\alpha_{IIb}$, $\alpha_L$, $\alpha_M$, $\alpha_X$) and $\beta$ subunits (e.g., $\beta_1$, $\beta_2$, $\beta^3$, $\beta^4$, $\beta_5$, $\beta_6$, $\beta_7$, and $\beta_8$)), K- FGF, LIF, leiomyoma-derived growth factor, MCP-1, macrophage-derived growth factor, monocyte-derived growth factor, MD-ECI, MECIF, MMP 2, MMP3, MMP9, urokinase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-$\beta$, PD-ECGF, PAI-2, PD-ECGF, PF4, P1GF, PKR1, PKR2, PPAR$\gamma$, PPAR$\gamma$ ligands, phosphodiesterase, prolactin, prostacyclin, protein S, smooth muscle cell-derived growth factor, smooth muscle cell-derived migration factor, sphingosine-1-phosphate-1 (S1P1), Syk, SLP76, tachykinins, TGF-$\beta$, Tie 1, Tie2, TGF-$\beta$ receptors, TIMPs, TNF-$\alpha$, TNF-$\beta$, transferrin, thrombospondin, urokinase, VEGF-A, VEGF-B, VEGF-C, VEGF-D, VEGF-E, VEGF, $VEGF_{164}$, VEGI, EG-VEGF, VEGF receptors, PF4, 16 kDa fragment of prolactin, prostaglandins E1 and E2, steroids, heparin, 1-butyryl glycerol (monobutyrin), and nicotinic amide. In other preferred embodiments, the matrix includes a chemotherapeutic agent or immunomodulatory molecule. Such agents and molecules are known to the skilled artisan. Preferably, the matrix includes bFGF, VEGF, or PDGF, or some combination thereof.

Regulation of HSC- and MSC-derived angiogenesis in engineered tissue grafts can be according to controlled release of growth factors. Engineered blood vessels can be "leaky" as a result of abnormally high permeability of endothelial cells. Maturation of human HSC-derived endothelial cells can be enhanced by micro-encapsulated delivery of angiogenic growth factors in progenitor cell-derived vascularized hybrid soft tissue implants implanted in vivo.

Biologic drugs that can be added to the compositions of the invention include immunomodulators and other biological response modifiers. A biological response modifier generally encompasses a biomolecule (e.g., peptide, peptide fragment, polysaccharide, lipid, antibody) that is involved in modifying a biological response, such as the immune response or tissue or organ growth and repair, in a manner which enhances a particular desired therapeutic effect, for example, the cytolysis of bacterial cells or the growth of tissue-specific cells or vascularization. Biologic drugs can also be incorporated directly into the matrix component. Those of skill in the art will know, or can readily ascertain, other substances which can act as suitable non-biologic and biologic drugs.

Biomolecules can be incorporated into the matrix, causing the biomolecules to be imbedded within. Alternatively, chemical modification methods may be used to covalently link a biomolecule on the surface of the matrix. The surface functional groups of the matrix components can be coupled with reactive functional groups of the biomolecules to form covalent bonds using coupling agents well known in the art such as aldehyde compounds, carbodiimides, and the like. Additionally, a spacer molecule can be used to gap the surface reactive groups in collagen and the reactive groups of the biomolecules to allow more flexibility of such molecules on the surface of the matrix. Other similar methods of attaching biomolecules to the interior or exterior of a matrix will be known to one of skill in the art.

Compositions of the invention can also be modified to incorporate a diagnostic agent, such as a radiopaque agent. The presence of such agents can allow the physician to monitor the progression of healing occurring internally. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents which can be utilized in the compositions of the invention can be readily ascertained by those of skill in the art and may include the use of radiolabeled fatty acids or analogs thereof.

The concentration of agent in the composition will vary with the nature of the compound, its physiological role, and desired therapeutic or diagnostic effect. A therapeutically effective amount is generally a sufficient concentration of therapeutic agent to display the desired effect without undue toxicity. A diagnostically effective amount is generally a concentration of diagnostic agent which is effective in allowing the monitoring of the integration of the tissue graft, while minimizing potential toxicity. In any event, the desired concentration in a particular instance for a particular compound is readily ascertainable by one of skill in the art.

The matrix composition can be enhanced, or strengthened, through the use of such supplements as human serum albumin (HSA), hydroxyethyl starch, dextran, or combinations thereof. The solubility of the matrix compositions can also be enhanced by the addition of a nondenaturing nonionic detergent, such as polysorbate 80. Suitable concentrations of these compounds for use in the compositions of the invention will be known to those of skill in the art, or can be readily ascertained without undue experimentation. The matrix compositions can also be further enhanced by the use of optional stabilizers or diluent. The proper use of these would be known to one of skill in the art, or can be readily ascertained without undue experimentation.

Implanting

The hybrid soft tissue implants of the invention hold significant clinical value because of their increased volume over other biological implants; minimization of donor site morbidity, allergic reactions, foreign body reactions, rapid resorption, and/or necrosis; and/or reduction of allergic reactions and/or foreign body reactions, which sets the compositions of the invention apart from other conventional treatment options. Thus the hybrid soft tissue implants and methods for their use described herein can circumvent issues associated with previous implant options using adipose progenitor cells and a synthetic biocompatible core to fabricate a hybrid soft tissue implant that is host friendly and relies on an abundant progenitor cell source.

A determination of the need for treatment will typically be assessed by a history and physical exam consistent with the tissue defect or disease at issue. Subjects with an identified need of therapy include those with a diagnosed tissue defect or disease. The subject is preferably an animal, including, but not limited to, mammals, reptiles, and avians, more preferably horses, cows, dogs, cats, sheep, pigs, and chickens, and most preferably human.

As an example, a subject in need may have soft tissue loss after trauma (including burns), congenital anomalies, chronic disease, or tumor resection. As another example, a subject in need can have undergone substantial loss of breast tissue through, for example, lumpectomy or mastectomy. As another example, a subject in need may have damage to a tissue, and the method provides an increase in biological function of the tissue. In a further example, the subject in need may have an increased risk of developing a disease, disorder, or condition that is delayed or prevented by the method.

The tissue or organ can be selected from breast, adipose, facial or elsewhere in the human body. The progenitor cells can be from the same subject into which the hybrid soft tissue implant is grafted. Alternatively, the progenitor cells may be from the same species, or even different species.

Implantation of a hybrid soft tissue implant is within the skill of the art. The matrix and cellular assembly can be either fully or partially implanted into a tissue of the subject to become a functioning part thereof. For example, one skilled in the art will understand that conventional techniques for the placement of conventional breast implants can be easily adapted for placement of the hybrid soft tissue breast implants described herein. Placement of breast implants is generally described in relation to the pectoralis major muscle. Examples of breast implant placement include, but are not limited to, subglandular (i.e., implant between the breast tissue and the pectoralis muscle); subfascial (i.e., in the subglandular position, but underneath the fascia of the pectoralis muscle); subpectoral (i.e., implant underneath the pectoralis major muscle after releasing the inferior muscular attachments); and submuscular (i.e., implant is placed below the pectoralis without release of the inferior origin of the muscle). Hybrid soft tissue breast implants for augmentation may be placed via various types of incisions including, but not limited to, inframammary, periareolar, transaxillary, transumbilical, or transabdominoplasty. It is understood that the subject may require one or more additional surgeries (reoperations) over the course of their lives. Reasons for reoperations include capsular contracture, wrinkling, asymmetry, rupture/deflation, implant malposition, and other local complications. Reoperation rates can be more frequent in breast reconstruction cases, particularly when patients have received, for example, external beam radiation treatment. Conventional breast implants are thought to require reoperation within five years for 1 in 3 women getting breast implants for reconstruction, while about 1 in 8 women getting breast implants for augmentation needed a reoperation within five years. As discussed above, these occurrences are reduced via the hybrid implant approached described herein.

Preferably, the hybrid implant initially attaches to and communicates with the host through a cellular monolayer contained within the adipose tissue outer coating which covers the acellular core material. Over time, the seeded cells can expand and migrate out of the polymeric matrix to the surrounding tissue. After implantation, cells surrounding the hybrid soft tissue implant can enter the biomaterial matrix through cell migration. The cells surrounding the engineered tissue can be attracted by biologically active materials, including biological response modifiers, such as polysaccharides, proteins, peptides, genes, antigens, and antibodies which can be selectively incorporated into the matrix to provide the needed selectivity, for example, to tether the cell receptors to the matrix or stimulate cell migration into the matrix, or both. Generally, the matrix is porous, having interconnecting microchannels and/or macrochannels that allow for cell migration, augmented by both biological and physical-chemical gradients. For example, cells surrounding the hybrid soft tissue implant can be attracted by biologically active materials including one ore more of VEGF, fibroblast growth factor, transforming growth factor-beta, endothelial cell growth factor, P-selectin, and intercellular adhesion molecule. One of skill in the art will recognize and know how to use other biologically active materials that are appropriate for attracting cells to the matrix.

The methods, compositions, and devices of the invention can include concurrent or sequential treatment with one or more of enzymes, ions, growth factors, and biologic agents, such as thrombin and calcium, or combinations thereof. The methods, compositions, and devices of the invention can include concurrent or sequential treatment with non-biologic and/or biologic drugs.

The application is additionally directed to the use of any of the above-described constructs for augmenting or reconstructing a soft tissue of a mammal.

Further, the application is directed to the use of any of the above-described constructs for the manufacture of a medicament for augmenting or reconstructing a soft tissue of a mammal.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

The following example describes engineering and implantation of adipose tissue constructs in a mouse model, where the implant retained original shape and dimensions.

Figure 2:
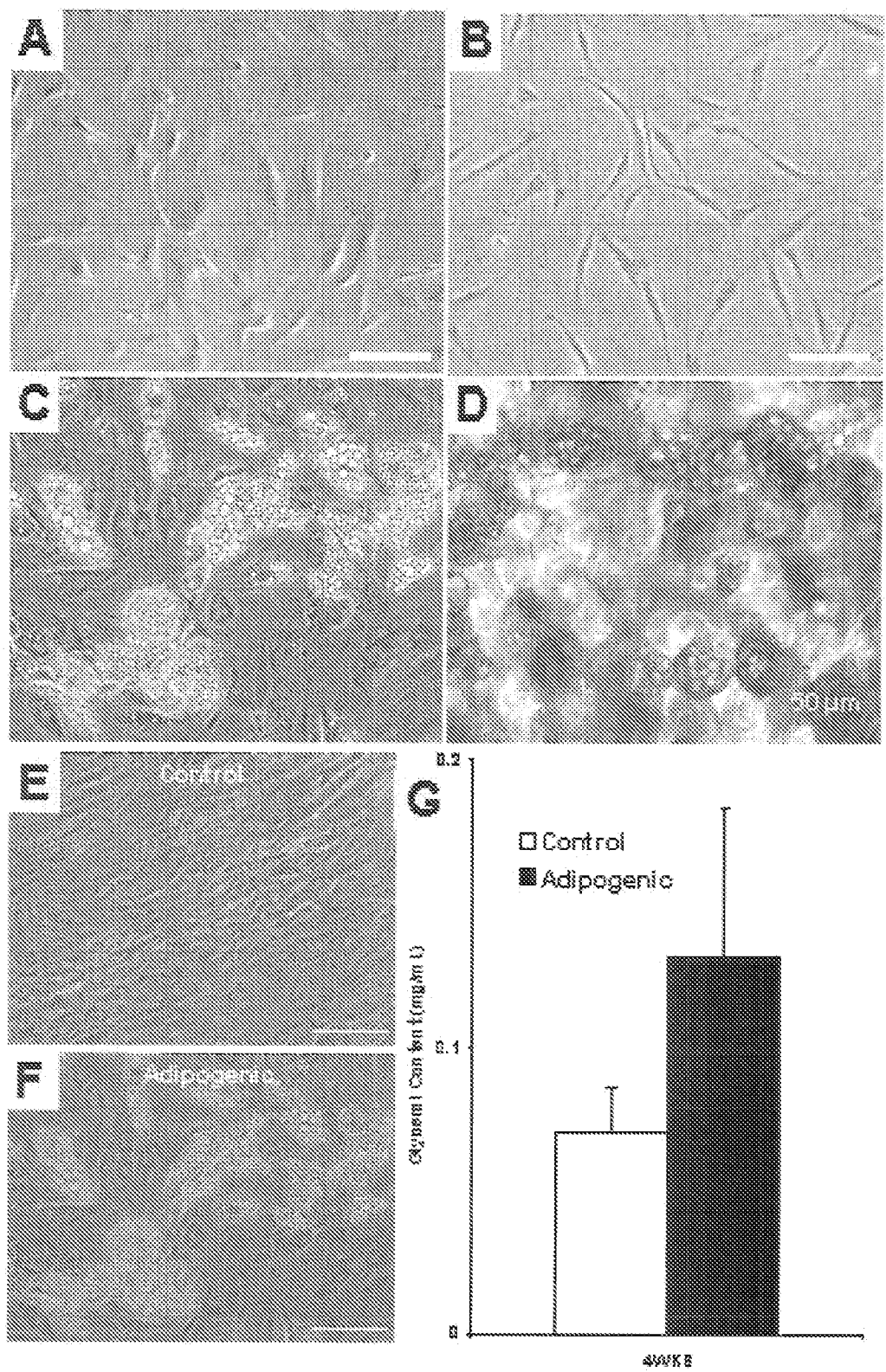
FIG. 2 is a series of micrographs and a graph depicting adipogenic differentiation of human bone marrow derived stem cells.

Human bone marrow derived stem cells (hMSCs) can differentiate into pre-adipocytes and adipocytes in vitro in both 2D and 3D. Four week culture of hMSCs (FIG. 2A, B) with adipogenic treated medium resulted in the progressive adipogenic differentiation as observed by the formation of lipid vacuoles in a percentage of the population of cells (FIG. 2C, D). Oil red-0 staining confirmed the lipid filled nature of these cells and quantification of glycerol content in adipogenic cultures compared to controls showed significant increase up to 4 weeks (FIG. 2E, F, G). Adipose tissue can be formed using bone marrow derived mesenchymal stem cells (MSCs) that are differentiated into pre-adipocytes and adipocytes in vivo (Alhadlaq et al. (2005)). Human MSCs were preconditioned by 1 week exposure to adipogenic-inducing supplements, photoencapsulated in preshaped polyethylene glycol diacrylate (PEGDA) hydrogels, and implanted subcutaneously in immunodeficient mice (Alhadlaq et al. (2005)). Four weeks after implantation, adipose tissue was observed by the visualization of lipids as wells as adipogenic marker gene expression. hMSCs that were not preconditioned with adipogenic supplements did not yield adipose tissue either in vitro or in vivo. The relatively short adipogenic conditioning time had significant effects in long-term engineered tissue development and fate. Importantly, the engineered adipose tissue retained the original shape and dimensions after 4 weeks implantation.

Example 2

The following example provides a technique for breast implant functionalization by fabricating a layer of adipose tissue from stem cells seeded in biocompatible hydrogels (polyethylene glycol diacrylate—PEGDA) to surround the acellular artificial core that provides the bulk of the implant.

The hybrid breast implant is composed of down-sized acellular PEGDA hydrogel (8 mL volume) (FIG. 3E) shaped like a commercially available silicone breast implant as the core (scale of 1:25=experimental implant volume:commercially available breast implant) and is surrounded by live adipose tissue seeded in photopolymerized PEGDA hydrogels (FIG. 3D-G).

To evaluate in vivo behavior of adipose tissue including angiogenesis and enzymatic activity, the engineered hybrid breast constructs is implanted subcutaneously in immunodeficient rats. This model allows for the implantation of human cells (xenograft) and demonstration of human adipose tissue engineering in vivo. It also demonstrates that acellular implants can be hybridized with live adipose tissue.

Figure 3:
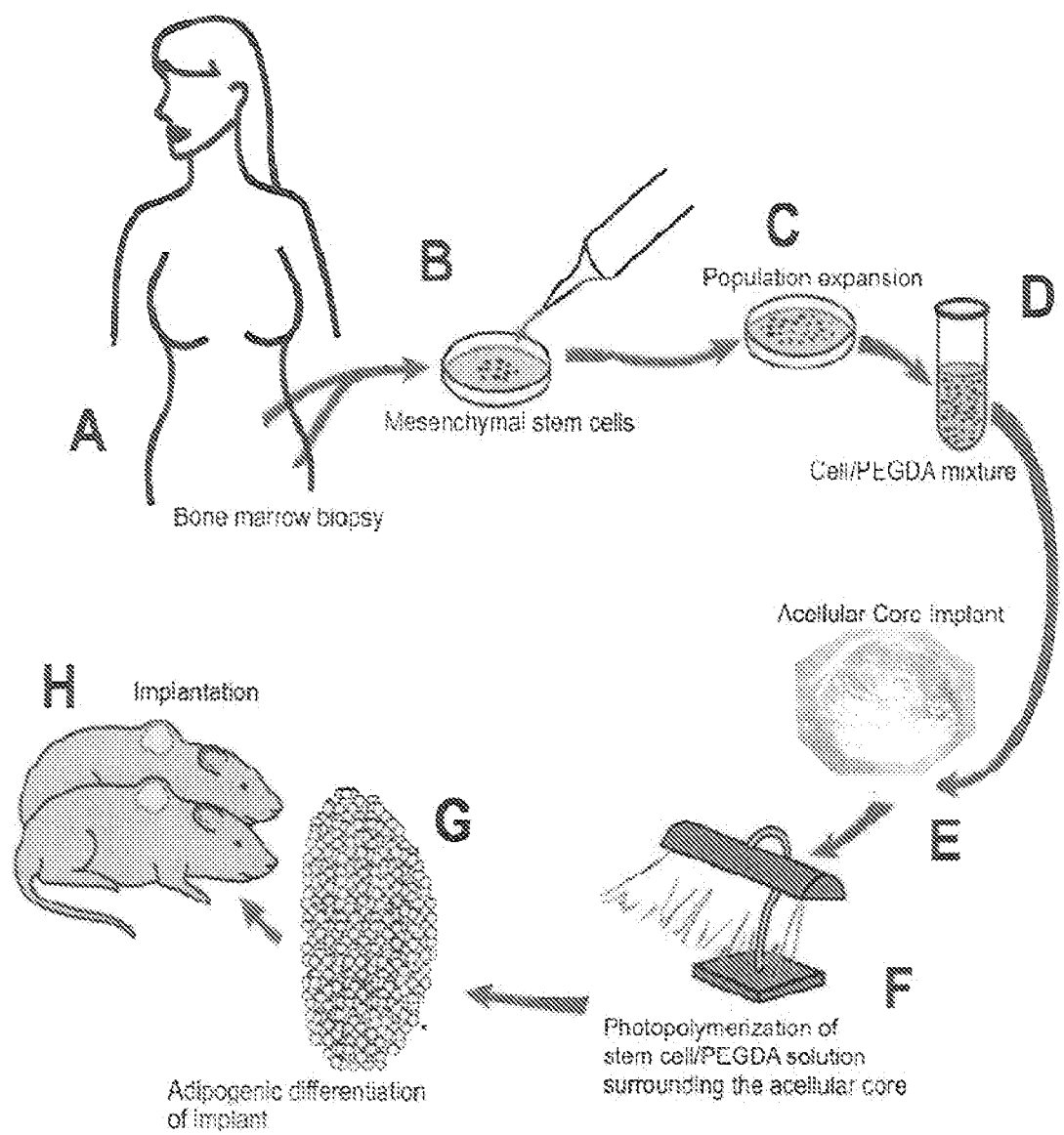
FIG. 3 is a diagram depicting fabrication and implantation of a hybrid soft tissue implant into a rat model system.

Human mesenchymal stem cells (hMSCs) are isolated from commercially available human bone marrow (AllCells, Emeryville, Calif.) as described in Alhadlaq and Mao (2005); and Moioli et al. (2006) (FIG. 3A, B). Human MSCs are culture expanded and seeded in PEGDA hydrogel solutions (liquid, pre-polymerization) (FIG. 3C, D). The pre-shaped acellular PEGDA hydrogel (FIG. 3E), which is the core of the implant is then submerged in the cell seeded hydrogel solution (FIG. 3D, E). Photopolymerization of the cell seeded outer region of the implant then takes place, completely surrounding the acellular hydrogel core (FIG. 3G). The resulting hybrid breast implant containing an acellular core and cellular periphery is then cultured in adipogenic medium to induce differentiation of stem cells into preadipocytes and adipocytes for 2 weeks per methods described in Alhadlaq et al. (2005). The adipogenic construct is then implanted subcutaneously in the dorsum immunodeficient rats and incubated for 2 or 4 weeks in vivo for the regeneration of adipose tissue surrounding the acellular core (FIG. 3H). The control group undergoes the same procedures but without cell seeding (entirely acellular implant lacking surrounding adipose tissue).

Example 3

The following example provides for the long-term viability requirements of adipose tissue for breast implants by the fabrication of vascularization tunnels that promote vascular network formation between the implant and the host, while promoting the formation of supporting connective tissue fibers that mimic the native suspensory ligaments of the breast, which are important for adipose tissue structural support.

Vascular channels are created in the hybrid breast implant. In order to accomplish this pre-designed architecture, capillary tubes of 0.9 mm outer diameter are placed radially around the implant during the submersion step of the acellular core implant into the cell seeded solution. The capillary tubes serve as temporary spacers and upon photopolymerization of the hybrid implant, the area in which the capillary tubes are, remains empty. Upon hardening (polymerization) of the implant, the capillary tubes are removed, leaving behind conduits extending from the outer region of the implant, deeper into the peripheral cellular portion, up to nearly the surface of the inner acellular core, but still not exposing the acellular core implant to the host (FIG. 4B). Previous studies have demonstrated that similar structures (macrochannels) in the same PEGDA hydrogel engineered construct induce host tissue invasion that carries vascular characteristics.

Example 4

A hybrid implant was fabricated as follows. The hybrid breast implant was composed of PEGDA (polyethylene glycol-diacrylate) hydrogel (3 mL volume) shaped like a commercially available silicone breast implant as the core, which was surrounded by live adipose tissue seeded in 2% alginate gel (2 mL volume). In order to evaluate in vivo behavior of adipose tissue, the engineered hybrid breast constructs were implanted subcutaneously in immunodeficient rats. This model allows for the implantation of human cells (xenograft) and demonstration of human adipose tissue engineering in vivo. It also addresses the proof of concept that acellular implants can be hybridized with live adipose tissue. Human mesenchymal stem cells (hMSCs) were isolated from human adipose tissue following IRB protocols of Columbia University. Human adipose tissue derived-MSCs (ASCs) were culture expanded and seeded in 2% alginate gel using calcium chloride as polymerizing agent to surround the acellular PEGDA core. The PEGDA core was previously polymerized using UV light. The resulting hybrid breast implant containing an acellular core and cellular periphery was then cultured in adipogenic medium to induce differentiation of stem cells into pre-adipocytes and adipocytes for 3 weeks. Controls underwent the same procedure, except that no cells were added to the alginate gel. The adipogenic construct was then implanted subcutaneously in immunodeficient rats and incubated for 4 weeks in vivo for the regeneration of adipose tissue surrounding the acellular PEGDA core.

Results.

Figure 5:
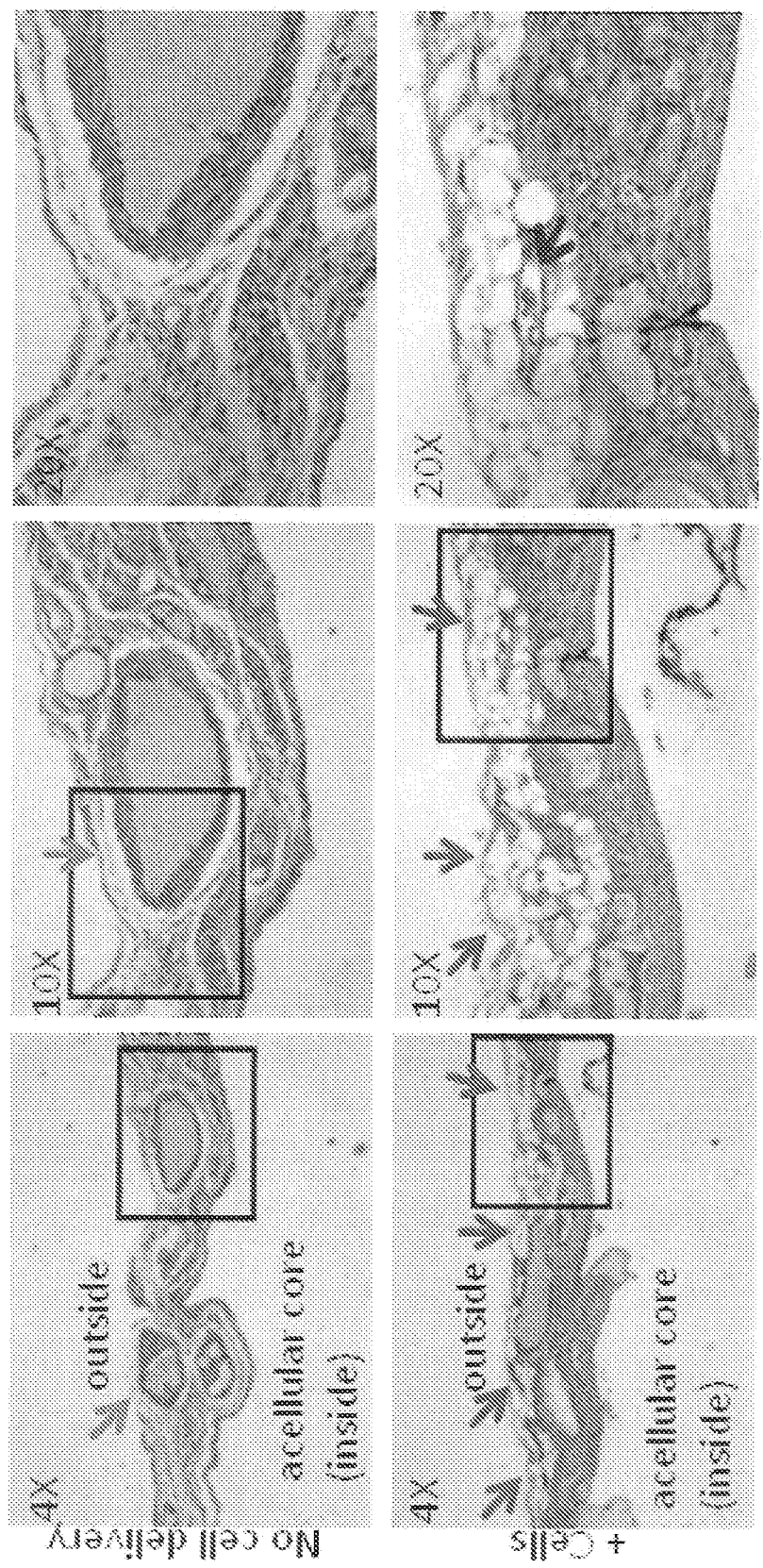
FIG. 5 is micrographs of a hematoxylin and eosin (H&E) stained control implant (top—no cells in implant) and an implant comprising cells surrounding an acellular core (bottom). Arrows in the top micrographs show a lack of adipose tissue; arrows in the bottom micrographs show adipose cells.
Figure 6:
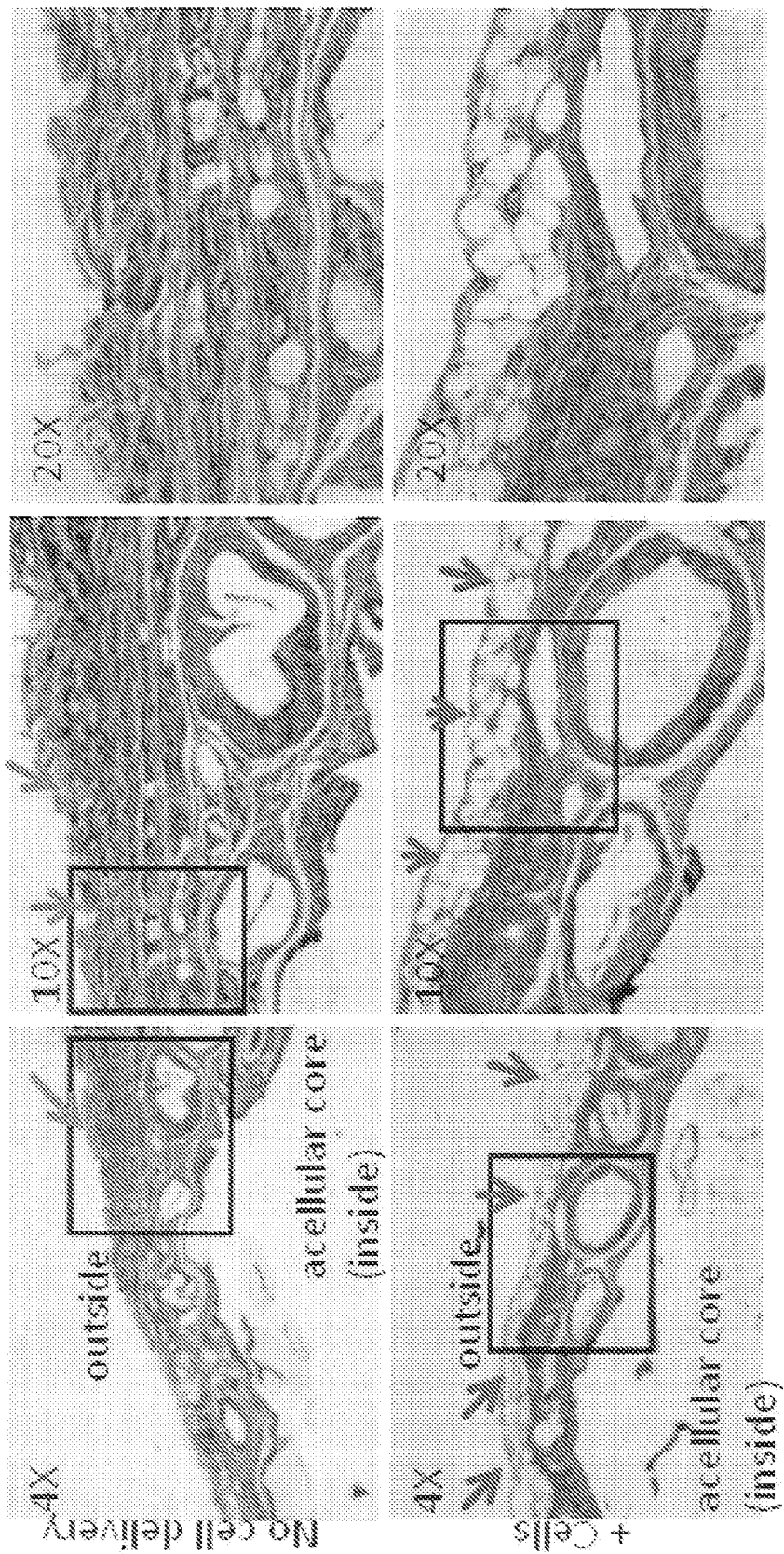
FIG. 6 is micrographs of a trichrome stained control implant (top—no cells in implant) and an implant comprising cells surrounding an acellular core (bottom). Arrows in the top micrographs show a fibrous/collagenous capsule; arrows in the bottom micrographs show adipose cells.

Four weeks after implantation, hybrid breast implants were harvested including surrounding tissue. The characteristic and nature of the surrounding capsule of the implant was evaluated. Hematoxylin and eosin (H&E) staining of cross sections indicated adipose tissue formation surrounding the acellular core of the implant (FIG. 5). Fat cells were clearly observed surrounding the implant, as well as blood vessels. In contrast, in the control group (no cells added), mostly fibrous tissue was observed with minimal fat-like tissue in the capsule. Trichrome staining of sections demonstrate a robust fibrous capsule around control implants (large dark-stained regions) indicating that the nature of the surrounding capsule is collagenous/fibrous (FIG. 6). On the other hand, cell-seeded hybrid implants resulted in a significant decrease in the fibrous capsule thickness (FIG. 6).

REFERENCES

Alhadlaq, A. & Mao, J. J. Mesenchymal stem cells: isolation and therapeutics. Stem Cells Dev. 13, 436-448 (2004).

Alhadlaq, A. & Mao, J. J. Tissue-engineered osteochondral constructs in the shape of an articular condyle. J Bone Joint Surg Am 87, 936-944 (2005).

Alhadlaq, A. et al. Adult stem cell driven genesis of human-shaped articular condyle. Ann Biomed Eng 32, 911-923 (2004).

Alhadlaq, A., Tang, M., & Mao, J. J. Engineered adipose tissue from human mesenchymal stem cells maintains predefined shape and dimension: implications in soft tissue augmentation and reconstruction. Tissue Eng 11, 556-566 (2005).

Alper, J. Biomedicine. New insights into type 2 diabetes. Science 289, 37-39 (2000).

Arnez, Z. M., Khan, U., Pogorelec, D., & Planinsek, F. Breast reconstruction using the free superficial inferior epigastric artery (SIEA) flap. Br. J Plast. Surg 52, 276-279 (1999a).

Arnez, Z. M., Khan, U., Pogorelec, D., & Planinsek, F. Rational selection of flaps from the abdomen in breast reconstruction to reduce donor site morbidity. Br. J Plast. Surg 52, 351-354 (1999b).

Aust, L. et al. Yield of human adipose-derived adult stem cells from liposuction aspirates. Cytotherapy. 6, 7-14 (2004).

Brown, S. L., Todd, J. F., & Luu, H. M. Breast implant adverse events during mammography: reports to the Food and Drug Administration. J Womens Health (Larchmt.) 13, 371-378 (2004).

Caplan, A. I. & Bruder, S. P. Mesenchymal stem cells: building blocks for molecular medicine in the 21st century. Trends Mol Med. 7, 259-264 (2001).

Chajchir, A. & Benzaquen, I. Liposuction fat grafts in face wrinkles and hemifacial atrophy. Aesthetic Plast. Surg 10, 115-117 (1986).

de la Fuente & Tavora, T. Fat injections for the correction of facial lipodystrophies: a preliminary report. Aesthetic Plast. Surg 12, 39-43 (1988).

Ferrara, ed. (2006) Angiogenesis, CRC, ISBN 0849328446.

Flassbeck, D. et al. Determination of siloxanes, silicon, and platinum in tissues of women with silicone gel-filled implants. Anal. Bioanal. Chem. 375, 356-362 (2003).

Goodwin, S. J. et al. Complications in smokers after postmastectomy tissue expander/implant breast reconstruction. Ann Plast. Surg 55, 16-19 (2005).

Huang, J. I. et al. Rat extramedullary adipose tissue as a source of osteochondrogenic progenitor cells. Plast. Reconstr. Surg 109, 1033-1041 (2002).

Jain et al. (2002) Nat. Rev. Cancer 2:266-276.

Jenkins, M. E., Friedman, H. I., & von Recum, A. F. Breast implants: facts, controversy, and speculations for future research. J Invest Surg 9, 1-12 (1996).

Lin, Y. et al. Multilineage differentiation of adipose-derived stromal cells from GFP transgenic mice. Mol Cell Biochem. 285, 69-78 (2006).

Ma and Elisseeff, ed. (2005) Scaffolding in Tissue Engineering, CRC, ISBN 1574445219.

Marion, N. W. and Mao, J. J. Mesenchymal stem cells and tissue engineering. Meth. Enzymol. 420, 339-361 (2006).

Matsudo, P. K. & Toledo, L. S. Experience of injected fat grafting. Aesthetic Plast. Surg 12, 35-38 (1988).

Minuth et al. (2005) Tissue Engineering: From Cell Biology to Artificial Organs, John Wiley & Sons, ISBN 3527311866.

Mizuno, H., Hyakusoku, H., Fujimoto, M., Kawahara, S., & Aoki, R. Simultaneous bilateral breast reconstruction with autologous tissue transfer after the removal of injectable artificial materials: a 12-year experience. Plast. Reconstr. Surg 116, 450-458 (2005).

Moioli, E. K., Hong, L., Guardado, J., Clark, P. A., & Mao, J. J. Sustained Release of TGFbeta3 from PLGA Microspheres and Its Effect on Early Osteogenic Differentiation of Human Mesenchymal Stem Cells. Tissue Eng 12, 537-546 (2006).

Niechajev, I. & Sevcuk, O. Long-term results of fat transplantation: clinical and histologic studies. Plast. Reconstr. Surg 94, 496-506 (1994).

Ogawa, R. et al. Osteogenic and chondrogenic differentiation by adipose-derived stem cells harvested from GFP transgenic mice. Biochem. Biophys. Res Commun. 313, 871-877 (2004a).

Ogawa, R. et al. Adipogenic differentiation by adipose-derived stem cells harvested from GFP transgenic mice-including relationship of sex differences. Biochem. Biophys. Res Commun. 319, 511-517 (2004b).

Pittenger, M. F. et al. Multilineage potential of adult human mesenchymal stem cells. Science 284, 143-147 (1999).

Patrick, C. W. Breast tissue engineering. Annu Rev. Biomed Eng 6, 109-130 (2004).

Patrick, C. W., Jr., Zheng, B., Johnston, C., & Reece, G. P. Long-term implantation of preadipocyte-seeded PLGA scaffolds. Tissue Eng 8, 283-293 (2002).

Saltzman (2004) Tissue Engineering: Engineering Principles for the Design of Replacement Organs and Tissues, Oxford ISBN 019514130X.

Shenaq, S. M. & Yuksel, E. New research in breast reconstruction: adipose tissue engineering. Clin. Plast. Surg 29, 111-25, vi (2002).

Shiffman, M. A. Silicone breast implant litigation (Part 1). Med. Law 13, 681-716 (1994).

Van, Z. D. & Heymans, O. Breast implants. A review. Acta Chir Belg. 104, 158-165 (2004).

Wong, C. H., Samuel, M., Tan, B. K., & Song, C. Capsular contracture in subglandular breast augmentation with textured versus smooth breast implants: a systematic review. Plast. Reconstr. Surg 118, 1224-1236 (2006).

Yoshimura, K. et al. Characterization of freshly isolated and cultured cells derived from the fatty and fluid portions of liposuction aspirates. J Cell Physiol 208, 64-76 (2006).

Zheng, B., Cao, B., Li, G., & Huard, J. Mouse adipose-derived stem cells undergo multilineage differentiation in vitro but primarily osteogenic and chondrogenic differentiation in vivo. Tissue Eng 12, 1891-1901 (2006).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of forming a hybrid soft tissue construct, the hybrid soft tissue construct comprising a core material, a biomaterial matrix, and isolated mammalian cells, the method comprising:
providing the isolated mammalian cells, the biomaterial matrix and the core material;
contacting the mammalian cells and the biomaterial matrix;
contacting the biomaterial matrix and the core material;
forming a plurality of macrochannels in the biomaterial matrix, the plurality of macrochannels not exposing the core material underlying the biomaterial matrix; and incubating the biomaterial matrix, the mammalian cells, and the core material to form the hybrid soft tissue construct;

wherein, the biomaterial matrix is a polyethylene glycol diacrylate (PEGDA) hydrogel further comprising the mammalian cells;

the hydrogel with the mammalian cells are contacted with the core material as a liquid then photopolymerized into a gel;

formation of the macrochannels comprises placing capillary tubes radially at locations near the core material before the core material and the hydrogel with the mammalian cells are contacted;

each of the capillary tubes is removed after the hydrogel with the mammalian cells contact the core material and after the hydrogel photopolymerizes into the gel;

the core material is acellular and biocompatible, and designed to remain acellular upon implantation in a subject;

the biomaterial matrix comprises a plurality of microchannel pores throughout the biomaterial matrix;

the plurality of macrochannels have an average diameter of 0.1 mm to 50 mm;

the plurality of macrochannels does not expose the core material to host tissue; and the biomaterial matrix contacts and covers the acellular core.

2. The method of claim 1, wherein the mammalian cells comprise adipose cells, interstitial cells, endothelial cells, smooth muscle cells, progenitor cells thereof, or a combination thereof.

3. The method of claim 1, wherein the mammalian cells comprise (i) adipose cells, (ii) progenitor cells selected from the group consisting of adipose tissue derived cells, pre-adipocytes, mesenchymal stem cells (MSC), MSC-derived cells, and adipocytes, or (iii) a combination thereof.

4. The method of claim 1, wherein the construct is a soft tissue implant for a breast, a face or a hand.

5. The method of claim 1, wherein the construct is a breast implant.

6. The method of claim 1, wherein the core material is (i) a saline or silicone gel implant, or (ii) a solid, high-cohesive, form-stable implant.

7. The method of claim 1, wherein the plurality of macrochannels have an average diameter of 2.5 mm to 50 mm.

8. The method of claim 1, wherein the biomaterial matrix comprises a growth factor selected from the group consisting of bFGF, VEGF and PDGF.

9. The method of claim 1, wherein the mammalian cells are present in the biomaterial matrix at a density of $0.0001 \times 10^6$ cells $ml^{-1}$ to $1000 \times 10^6$ cells $ml^{-1}$.

10. The method of claim 1, wherein the mammalian cells comprise a first progenitor cell and a second progenitor cell, the first progenitor cell is an adipose progenitor cell, and the second progenitor cell is a vascular progenitor cell.

11. The method of claim 1, wherein a layer comprising isolated adipose cells covers the core material.

12. The method of claim 1, wherein incubation occurs in vitro.

13. The method of claim 1, wherein incubation occurs in vivo.

14. The method of claim 1, wherein incubation occurs in vitro and in vivo.

15. The method of claim 1, wherein the acellular core material has a volume of $0.5$ $cm^3$ to $100$ $cm^3$.

16. The method of claim 1, the core material is selected from the group consisting of an artificial implant material, a breast implant material, a saline implant, a silicone gel implant, a multiple lumen design implant, a gummy bear implant, a solid implant, a high-cohesive implant, and a form-stable implant; and the core material is suitable to be functionalized by surrounding autologous engineered adipose tissue from progenitor cells.

17. The method of claim 1, further comprising coating the core material with an elastomer or polyurethane foam.

* * * * *